(12) United States Patent
Motamedi

(10) Patent No.: US 9,610,009 B2
(45) Date of Patent: Apr. 4, 2017

(54) DENTAL RETRACTOR FOR PROTECTING A PATIENT'S TEETH FROM CONTACT WITH THE INNER SIDE OF A PATIENT'S MOUTH AND TONGUE

(71) Applicant: Shohreh Motamedi, Baltimore, MD (US)

(72) Inventor: Shohreh Motamedi, Baltimore, MD (US)

(*) Notice: Subject to any disclaimer, the term of this patent is extended or adjusted under 35 U.S.C. 154(b) by 144 days.

(21) Appl. No.: 14/541,183

(22) Filed: Nov. 14, 2014

(65) Prior Publication Data

US 2015/0140506 A1    May 21, 2015

Related U.S. Application Data

(60) Provisional application No. 61/904,558, filed on Nov. 15, 2013.

(51) Int. Cl.
| | |
|---|---|
| *A61C 1/00* | (2006.01) |
| *A61B 1/247* | (2006.01) |
| *A61C 5/14* | (2006.01) |

(52) U.S. Cl.
CPC ............ *A61B 1/247* (2013.01); *A61C 5/14* (2013.01)

(58) Field of Classification Search
CPC .................................. A61B 1/247; A61C 5/14
See application file for complete search history.

(56) References Cited

U.S. PATENT DOCUMENTS

| | | |
|---|---|---|
| 4,511,329 A | 4/1985 | Diamond |
| 5,490,780 A | 2/1996 | Riewenherm |
| 6,267,591 B1 | 7/2001 | Barstow |
| 6,837,707 B2 | 1/2005 | Figueredo Torres |
| 7,217,241 B2 | 5/2007 | Guenier et al. |
| 7,553,158 B2 | 6/2009 | Frider et al. |
| 8,323,021 B2 | 12/2012 | Fishburne, Jr. |
| 2010/0304324 A1* | 12/2010 | Dragan ............ A61C 5/14 433/31 |

* cited by examiner

*Primary Examiner* — George Manuel
(74) *Attorney, Agent, or Firm* — Hauptman Ham, LLP

(57) ABSTRACT

A dental retractor for preventing a patient's teeth from contact with an inner portion of a patient's mouth and tongue. The retractor includes three members. A first plate like member is constructed and dimensioned to fit between a patient's teeth and the inner side of the patient's cheek. A second plate like member is constructed and dimensioned to fit between the patient's same teeth and the patient's tongue. A third rod-shaped member connects the first and second members and is integral therewith and connected to a central portion thereof with mirrors. A mirror surface on one of the first and second members facing the teeth is provided.
In a further embodiment of the invention, the first member fits between the upper and lower teeth on both sides of the mouth and includes a mirror for inspecting essentially all of a patient's teeth.

6 Claims, 4 Drawing Sheets

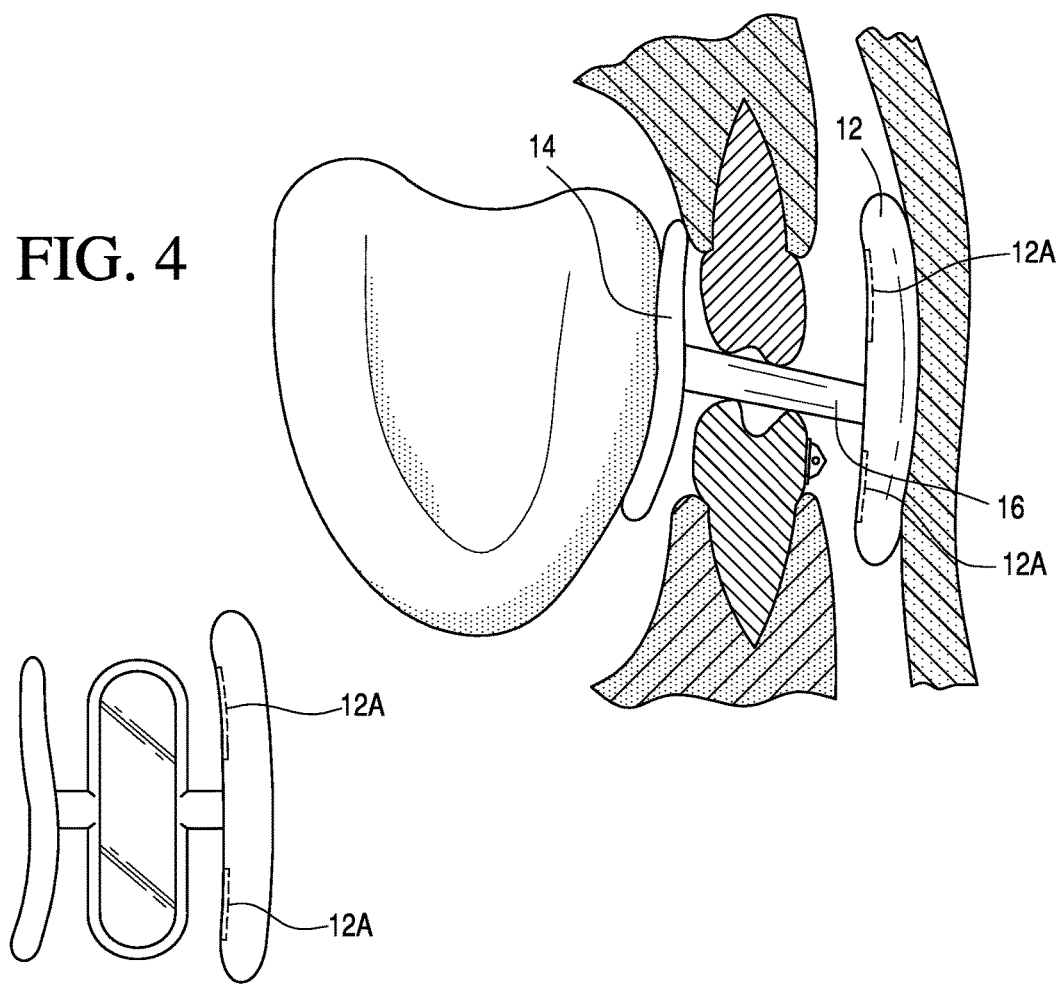
FIG. 4
FIG. 4A
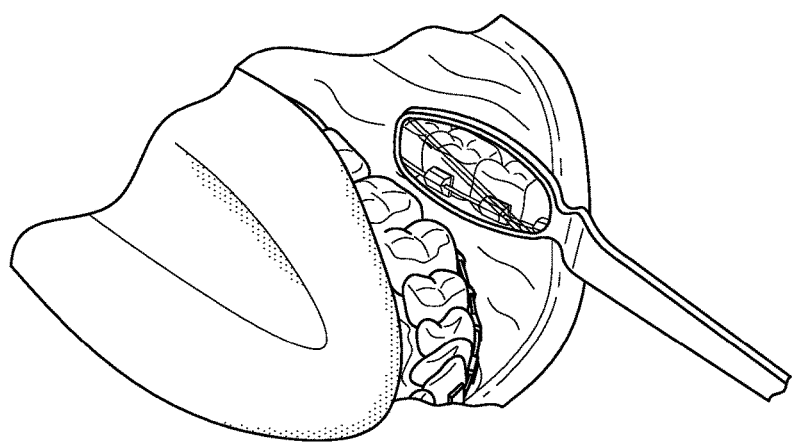
FIG. 5
PRIOR ART

DENTAL RETRACTOR FOR PROTECTING A PATIENT'S TEETH FROM CONTACT WITH THE INNER SIDE OF A PATIENT'S MOUTH AND TONGUE

FIELD OF THE INVENTION

This invention relates to a dental retractor for maintaining a tooth or a plurality of teeth in a dry condition by maintaining the tooth or teeth free from contact with an inner portion of a patient's mouth and tongue.

BACKGROUND FOR THE INVENTION

Dental retractors have been used in general dentistry for many years to keep the cheek away from a tooth or teeth, for tooth (teeth) extractions. They have also traditionally been used by orthodontists to prevent saliva from contacting a tooth or teeth when bonding metal bands and/or metal/ceramic brackets to the teeth. However, such retractors have limitations due to the following reasons: decreased comfort due to complex designs, limited visibility, and at the same time still allow saliva to contact teeth. This results in failure of cement adhesion, increases the likelihood of loose bands, broken brackets and/or fillings. This results in increased time and expense for orthodontists, dentists and the patients.

A dental lip retractor is disclosed in a Ghim U.S. Pat. No. 6,964,570. As disclosed, the retractor comprises a substantially U-shaped strip and an elongated handle. The U-shaped strip has a top edge and a bottom edge. Each of the edges form a substantially U-shape and wherein the U-shape formed by the bottom edge is smaller than the U-shaped formed by the top edge. The elongated handle has a distal end of the handle attached to the U-shaped strip at a substantially trough point of the U-shaped strip.

A more recent Fishburne, Jr. U.S. Pat. No. 8,323,021 discloses a dental bilateral bite block of sheet material having a central body portion with attached wings capable of folding toward each other on each side of the central body portion. The wings of the bite block fold toward each other along fold lines adjacent the central body portion and provide a structure for propping the mouth of a patient open during a dental procedure. A mirrored surface may be placed on the central body portion for improved visibility. The bite block also holds or retracts the tongue and cheeks away from a work area.

The present invention can be used in general dentistry and in orthodontic procedures. It is believed that the retractors in accordance with the present invention will free up one of a dentist's or orthodontist's hands by eliminating the need for a handheld mirror and constant need for repositioning the handheld mirror.

In many cases, this should make a dentist or orthodontist more efficient, lead to more patients and larger profits as well as additional user time. For general dentists, the retractors in accordance with the present invention may be used for many different procedures.

Notwithstanding the above, it is presently believed that there is a need and a potential commercial market for an improved dental retractor for maintaining a tooth or a plurality of teeth in a dry condition. It is believed that there is a need and a potential market for such devices because they protect a tooth or a plurality of teeth from being in contact with an inner portion of the patient's cheek and tongue. The invention can also be used by endodontist for root canals as well as by periodontist for surgical procedures.

The dental retractor in accordance with the present invention also provides an improved visual view of up to 5 or 6 teeth and enables an orthodontist or his or her assistant to have a clear view to bond metal or ceramic brackets to one or more teeth. Each bracket or band is cemented to a tooth and it is imperative that the surface of the tooth is dry in order to obtain a satisfactory bond between a band or bracket and a tooth. Therefore, it is very important that a tooth is not touched by the inside of a patient's mouth or tongue.

In addition, it is desirable to provide a comfortable retractor for a patient and to avoid the complex retractors of the prior art. Still further, it is desirable to provide a low cost device of minimal complexity.

SUMMARY OF THE INVENTION

In essence, a dental retractor for protecting a patient's tooth or teeth from contacting an inner side of a patient's mouth and tongue comprises or consists of a first relatively thin mirror or member that is constructed and dimensioned to fit between a patient's teeth and an inner side of a patient's mouth i.e. cheek. The retractor also includes a second relatively thin plate like body or member constructed and dimensioned to fit between said teeth and the patient's tongue and a third member connecting the first and second members. A mirrored surface is provided on one of said first and second members facing the teeth.

In one embodiment of the invention, the first and second member have a height and width of between 1 inch and 2 inches and a thickness of between $\frac{1}{8}$ inch and $\frac{5}{8}$ inch and said third member having a rod like shape made of double sided mirrors with a thickness of about $\frac{1}{8}$ inch to $\frac{5}{8}$ inch. The preferred embodiment of the invention is made of a hard non-toxic plastic such as polypropylene (PP), polyethylene terephthalate (PET) or other suitable plastic such as acrylonitrile butadiene styrene (ABS). In this embodiment, a pair of slightly inclined toward one another mirrors are focused on one or several teeth and may be used to examine at least four teeth while the mouth and inner cheek engaging portions have a smooth curved surface that is free from sharp edges or projections.

In a preferred embodiment of the invention, a first member fits between the upper and lower teeth on both sides of a patient's mouth and includes a mirror like surface for inspecting essentially all of the patient's teeth.

In a further embodiment of the invention, a mirror shows the rear portion of a patient's front teeth.

The invention will now be described in connection with the accompanying drawings wherein like elements are identified with like numbers.

DESCRIPTION OF THE DRAWINGS

FIG. 4 is a schematic illustration of a dental retractor according to the invention separating at least four posterior teeth from an inside of the patient's mouth and tongue;

FIG. 4a illustrates a modification of the first embodiment of the invention that includes a mirror on the top and bottom of a cross member;

FIG. 5 is a schematic illustration of a handheld mirror held in place adjacent to a patient's teeth;

DESCRIPTION OF THE PREFERRED EMBODIMENTS OF THE INVENTION

Figure 1:
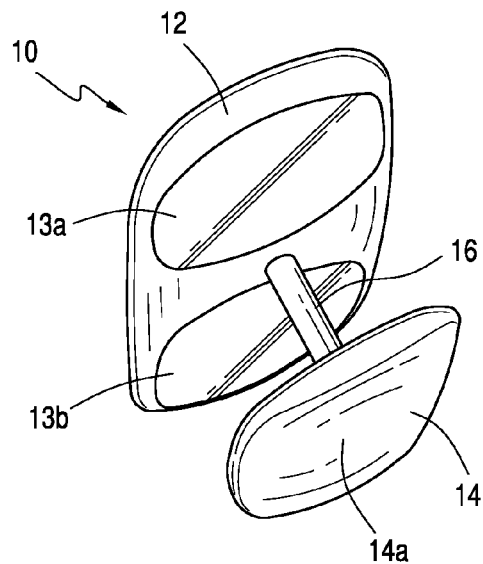
FIG. 1 is a perspective view of a dental retractor according to a first embodiment of the invention wherein the retractor is for viewing and keeping the posterior (back) teeth dry.
Figure 2:
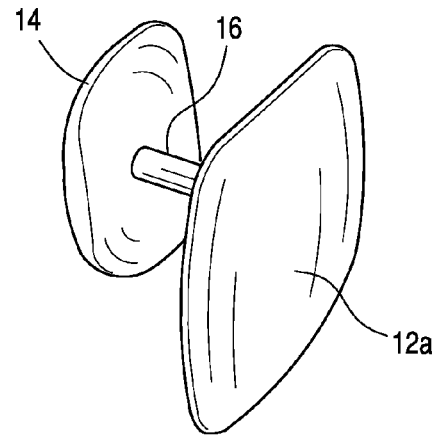
FIG. 2 is a perspective view of the dental retractor shown in FIG. 1 but taken from an opposite direction.

As illustrated in FIGS. 1-4 a dental retractor in accordance with a preferred embodiment of the invention comprises or consists of an integral body or retractor 10. As illustrated, the body or retractor 10 includes a first member 12 for separating a patient's tooth or plurality of teeth from contact with an inner portion of a patient's mouth as for example, an inner portion of a patient's cheek.

In a number of dental procedures, it is necessary to dry a tooth or portion thereof and to maintain the tooth or portion thereof in a dry condition during a dental procedure. For example, in orthodontics, when bonding (gluing) braces on a patient's teeth it is imperative that the teeth stay completely dry. Otherwise the bracket (brackets) will fall off. Bond failure is the nemesis to every orthodontists practice. Each bracket that comes off will cause an orthodontist up to $26.00. There is the costs of the orthodontists time, the assistants time, costs of a new bracket or brackets depending how many have come off and material needed to place the bracket/brackets back on. This is an ongoing problem that every orthodontists deals with ¼ to ⅓ of his patients each day.

The small metallic or ceramic brackets are commonly glued to a tooth and if contaminated with moisture no adhesive bond will be established. The problem is that the inner portion of a patient's mouth constantly produces body fluids or saliva. It is common practice to use cotton to absorb saliva and compressed air in an attempt to maintain a tooth in a dry condition. However, contact between the tooth and inner portion of the mouth or tongue will undermine that effort. Consequently, dental retractors have been designed to isolate one or more teeth from contact by or with an inner portion of a patient's mouth or tongue.

In a first embodiment of the invention, a first member 12 has a generally plate like structure with a generally rectangular, square, oval or circular shape having a height and/or width of about 1 to 2 inches and a thickness of about ⅛ inch to ⅝ inch with a flat or nearly flat surface facing an outer (buckle) surface of the tooth or several teeth. In a preferred embodiment of the invention, the flat surface includes a mirrored surface or one or two separate mirrors on the flat surface. In the case of multiple mirrors, the mirrors are one above the other with a slight angular inclination so that they are focused on one or the same series of teeth. It is also contemplated that the flat surface may be slightly curved so that the mirrored surface reflects an image of several teeth in a single row of teeth or a portion of a dental arch.

The body 10 includes a second plate like member 14 of about the same or smaller size and general shape of the first member 12. The general shape of the first member and the second member 14 is constructed and dimensioned to fit between the patient's teeth and the patient's tongue to prevent a dry tooth from being contacted by the patient's tongue or cheek.

A third member 16 connects the first and second members 12 and 14 in a generally parallel fixed spaced apart relationship at a distance of about ¾ to about 1¼ inches. This member has mirrors on top and bottom of the connecting member 16 between members 12 and 14 facing away from each other. The top mirror will show the occlusions (chewing surface) of the upper posterior teeth and the bottom mirror shows the occlusions of the lower posterior teeth. In the preferred embodiment of the invention the first, second and third members are integrally formed of a relatively hard plastic composition selected from the group consisting of polypropylene (PP), polyethylene terephthalate (PET) and acrylonitrile butadiene styrene (ABS) and the like.

It is also contemplated that the third member 16 may have an enlarged portion or bite block 17 formed as an integral part of the member 16. The bite block positions the mouth and the dental retractor for installing the brackets. In the preferred embodiment of the invention, the inner surface that is the surface facing an outer portion of the tooth is flat and contains a mirror surface for reflecting an image of a portion of a patient's teeth.

Figure 3:
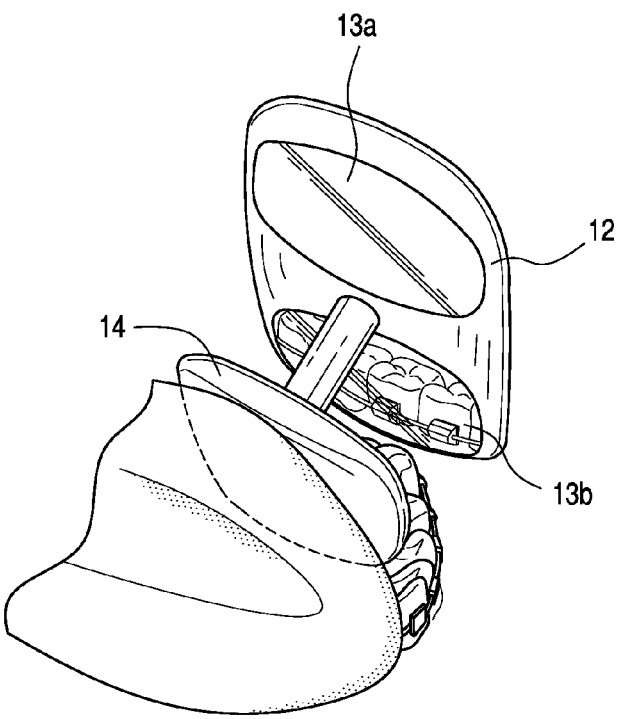
FIG. 3 is a perspective view of the dental retractor shown in FIGS. 1 and 2 positioned inside a patient's mouth.

As more clearly in FIGS. 1 and 3, the first member 12 includes one or two mirrors 13a and 13b on an inner side 12a thereof.

As illustrated more clearly in FIG. 4, the first member 12 has a slightly curved relatively smooth convex surface 12c that is free of sharp edges or projections. As shown, the surface 12c engages an inner portion of the patient's cheek and prevents the inner portion of the patient's cheek from contacting a dry tooth or teeth. In a similar manner, a tongue engaging portion 14a has a slightly curved convex smooth surface that engages the patient's tongue and prevents the tongue from contacting the tooth under examination or being worked on.

A second embodiment of the invention should have broad appeal to dental professionals and technicians who work in the dental field. However, unlike conventional dental retractors, this new retractor should have broad appeal to general dentists, hygienists, endodontists, periodontists and technicians. Such retractors should appeal to general dentists because they can replace the need for a handheld mirror, keep the desired tooth dry, free up one hand of a dentists or technician and should lead to a more efficient and speedy practice.

Figure 6:
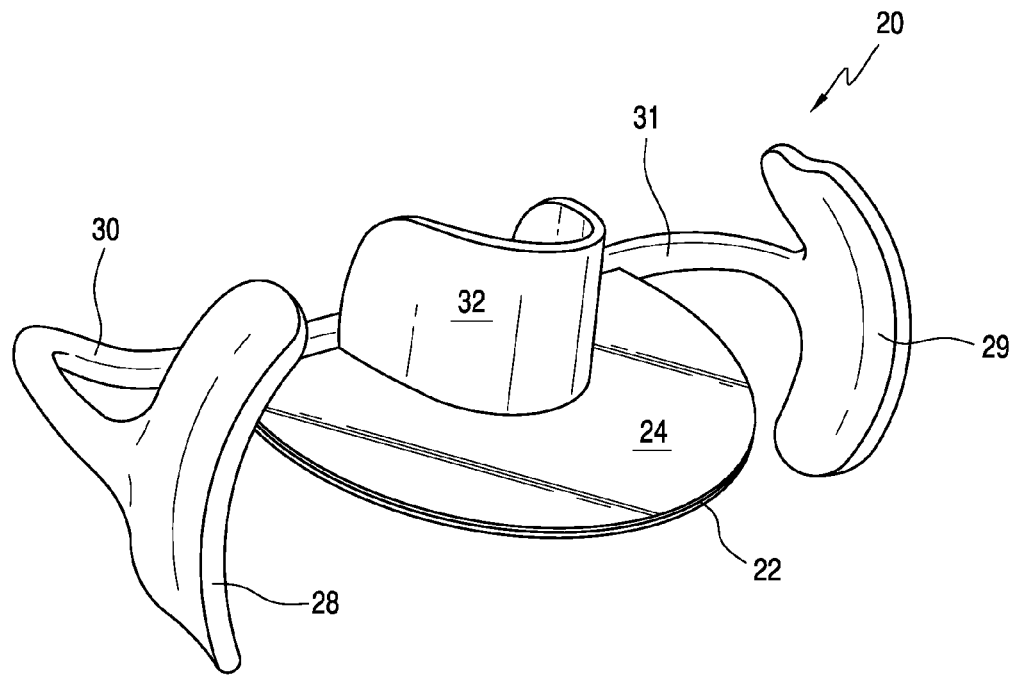
FIG. 6 is a perspective view illustrating the preferred embodiment of the invention.
Figure 7:
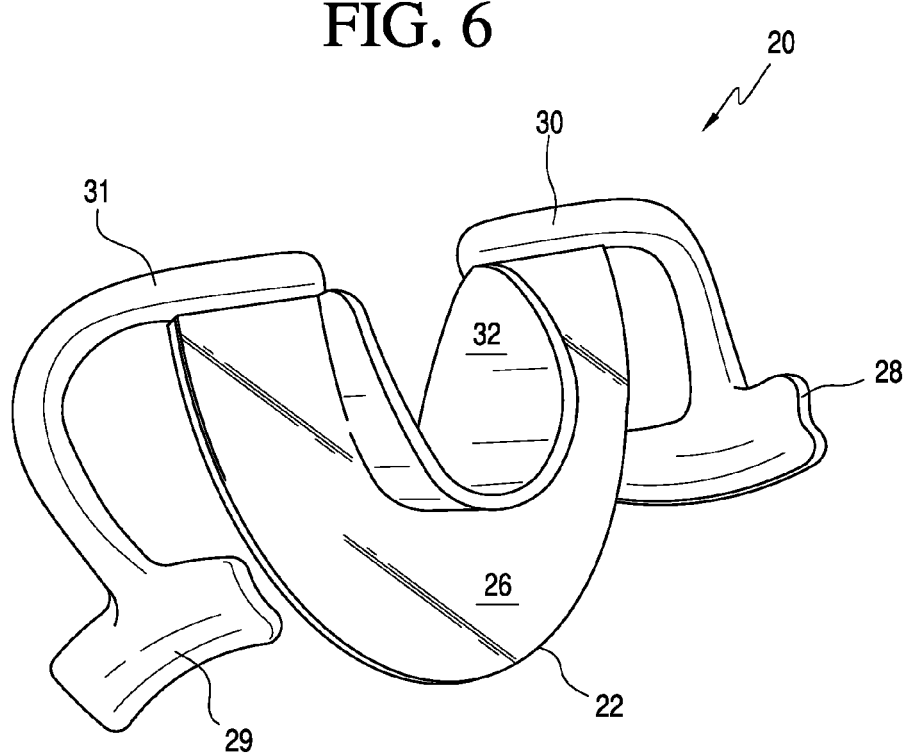
FIG. 7 is a perspective view looking at the underside of a dental retractor as illustrated in FIG. 6.

In essence the dental retractor 20 as shown in FIGS. 6 and 7 protect a patient's teeth from contact with an inner side of a patient's mouth and tongue. The retractor 20 comprises or consists of a first member and more specifically a general U-shaped flat plate like member 22 having an upper and a lower surface that is constructed and dimensioned to fit between essentially all of a patient's upper teeth and essentially all of the patient's lower teeth.

As illustrated, the retractor 20 includes a U-shaped upper surface 24 (FIG. 6) as well as two reflective sides on the upper surface 24 and on the lower surface 26. It is contemplated that both surfaces will be covered by a mirrored surface.

The retractor 20 also includes a pair of upwardly extending cheek retractors 28 and 29 that fit between an inner portion of a patient's cheeks and the upper and lower teeth on each side of the patient's mouth. As shown, the cheek retractors 28 and 29 extend upwardly and downwardly from a pair of arms 30 and 31 that are connected to or integral with a central member or tongue retractor 32. The cheek retractor as well as the arms 30 and 31 may have different shapes and different sizes to accommodate different patients as for example for a child and an adult.

Figure 8:
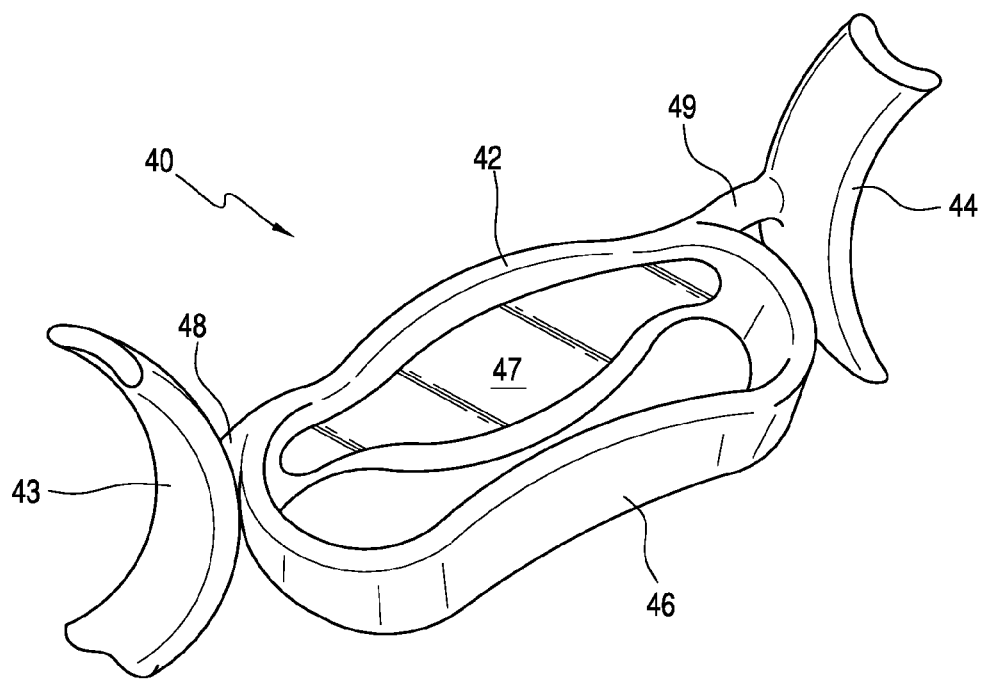
FIG. 8 is a perspective view of an additional embodiment of a dental retractor in accordance with the invention for bonding lingual braces and lingual retainers.
Figure 9:
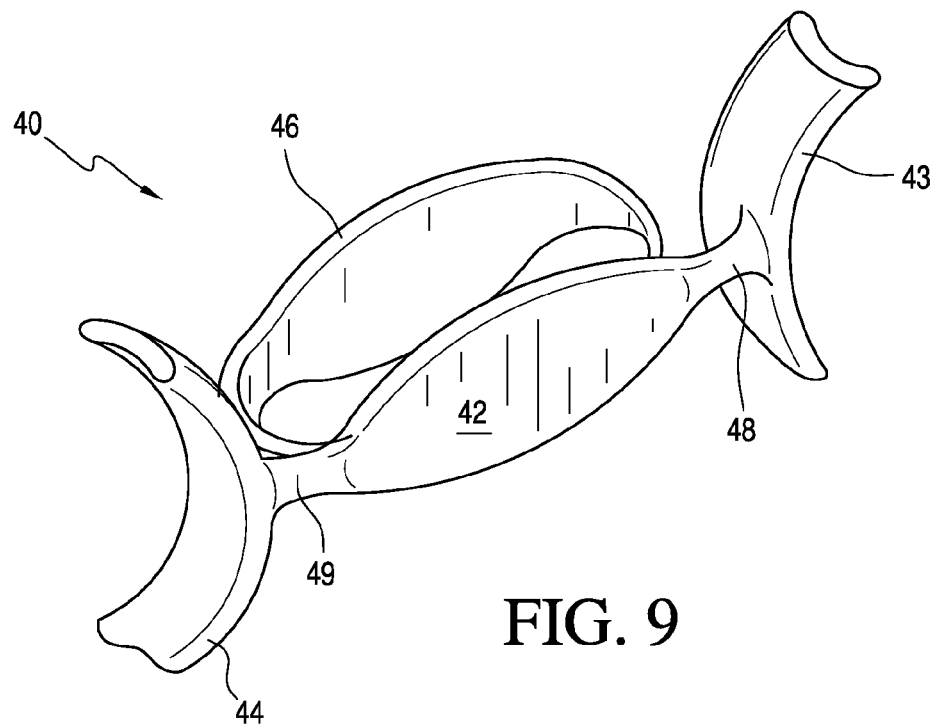
FIG. 9 is a perspective view of the dental retractor shown in FIG. 8.

A further embodiment of the invention illustrated in FIGS. 8 and 9. As illustrated, a dental retractor 40 includes a first member 42 and a pair of cheek retractors 43 and 44 connected to or integral with the first member 42. The cheek retractors extend upwardly and downwardly but may be made in different shapes and sizes. It is contemplated that the dental retractor 40 like retractors 10 and 20 will be made of a one piece injection molded relatively hard plastic such as polypropylene (PP), polyethylene terephthalate (PET) or the like.

The dental retractor 40 in accordance with the third embodiment of the invention also includes a tongue retractor 42 that extends across a patient's mouth behind the dental arch or front teeth. The third embodiment of the invention also includes a mirror 47 facing behind the front teeth of a patient as well as a pair of arms 48 and 49 connected to the member 42 for supporting the cheek retractors 43 and 44.

While the invention has been described in connection with its preferred embodiments, it should be recognized that changes and modifications may be made therein without departing from the scope of the appended claims.

What is claimed is:

1. A dental retractor for protecting a patient's teeth against contact with an inner side of a patient's cheek and tongue, said retractor consisting of:
    a first member constructed and dimensioned to fit between a patient's teeth and an inner side of a patient's cheek, a second member constructed and dimensioned to fit between said teeth and the patient's tongue and wherein said first and said second member each have a height and width between 1 and 2 inches and a thickness of between 1/8 inch and 5/8 inch and in which said first and second members have a plate like construction and are generally parallel to each other and said third member has the shape of a rod with a thickness of about 3/8 inch and wherein said first, second and third members are an integral body of non-toxic plastic material with a mirror surface on one of said first and second members facing a tooth and said third member is perpendicular with said first and second members.

2. The dental retractor for protecting a patient's teeth against contact with an inner side of a patient's cheek and tongue according to claim 1, which includes a second mirror adjacent to said first mirror surface with a slight deviation to focus on the same tooth or teeth as said first mirror.

3. A dental retractor for protecting a patient's teeth from contact with an inner side of a patient's mouth and tongue according to claim 1, in which said third member includes a pair of mirrors one facing the top and the other facing the bottom of a patient's posterior teeth.

4. A dental retractor for protecting a patient's teeth from contact with an inner side of a patient's mouth and tongue, said retractor consisting of:
    a generally flat U-shaped member having an upper and a lower surface and constructed and dimensioned to fit between essentially all of a patient's upper teeth and essentially all of a patient's lower teeth and extending outwardly therefrom;
    a reflective surface on each of said upper and said lower surfaces of said U-shaped member;
    a pair of cheek retractors for separating an inner portion of said cheeks from the patient's teeth; and
    a generally U-shaped tongue retractor separating the patient's tongue from the patient's teeth disposed between said pair of cheek retractors adjacent said U-shaped first member and abutting an inner portion of said U-shaped reflective surface.

5. A dental retractor for protecting a patient's teeth from contact with an inner side of a patient's mouth and tongue, said retractor consisting of:
    a first member including a mirror constructed and dimensioned to be positioned outwardly behind a patient's front teeth;
    a pair of cheek retractors for separating inner portions of a patient's cheeks from contact with a patient's teeth; and
    a U-shaped tongue retractor connected to said first member and constructed and dimensioned to fit across a patient's teeth behind patient's dental arch and between the upper and lower teeth on both sides of a patient's mouth.

6. A dental retractor for protecting a patient's teeth from contact with an inner side of a patient's mouth and tongue, said retractor comprising:
    a generally flat U-shaped member having an upper and a lower surface and constructed and dimensioned to fit between essentially all of a patient's upper teeth and essentially all of a patient's lower teeth and extending outwardly therefrom;
    a reflective surface on each of said upper and said lower surfaces of said U-shaped member;
    a pair of cheek retractors for separating an inner portion of said cheeks from the patient's teeth; and
    a generally U-shaped tongue retractor separating the patient's tongue from the patient's teeth disposed between said pair of cheek retractors adjacent said U-shaped first member and abutting an inner portion of said U-shaped reflective surface.

\* \* \* \* \*